United States Patent
Jacobs

(10) Patent No.: US 8,672,981 B2
(45) Date of Patent: Mar. 18, 2014

(54) OSTEOSYNTHESIS PLATE COMPRISING THROUGH-OPENINGS WHICH ARE INCLINED IN RELATION TO THE PLANE OF THE PLATE

(75) Inventor: Fred J. Jacobs, Pretoria (ZA)

(73) Assignee: Stryker Leibinger GmbH & Co. KG., Freiburg (DE)

( * ) Notice: Subject to any disclaimer, the term of this patent is extended or adjusted under 35 U.S.C. 154(b) by 454 days.

(21) Appl. No.: 11/988,225

(22) PCT Filed: Jun. 30, 2006

(86) PCT No.: PCT/EP2006/006365
§ 371 (c)(1),
(2), (4) Date: Apr. 10, 2009

(87) PCT Pub. No.: WO2007/006430
PCT Pub. Date: Jan. 18, 2007

(65) Prior Publication Data
US 2009/0318920 A1 Dec. 24, 2009

(30) Foreign Application Priority Data
Jul. 8, 2005 (DE) .......................... 10 2005 032 026

(51) Int. Cl.
*A61B 17/80* (2006.01)
(52) U.S. Cl.
USPC ........................................ 606/280; 606/904
(58) Field of Classification Search
USPC .................................. 606/280, 902
See application file for complete search history.

(56) References Cited

U.S. PATENT DOCUMENTS

| | | | |
|---|---|---|---|
| 4,683,878 A * | 8/1987 | Carter | 606/97 |
| 5,549,612 A | 8/1996 | Yapp et al. | |
| 5,558,674 A | 9/1996 | Heggeness et al. | |
| 6,325,803 B1 | 12/2001 | Schumacher et al. | |
| 6,364,881 B1 | 4/2002 | Apgar et al. | |
| 6,423,068 B1 | 7/2002 | Reisberg et al. | |
| 2002/0128654 A1* | 9/2002 | Steger et al. | 606/69 |
| 2005/0261688 A1* | 11/2005 | Grady et al. | 606/69 |

FOREIGN PATENT DOCUMENTS

| | | |
|---|---|---|
| DE | 9208234.3 | 6/1992 |
| DE | 19636733 | 9/1996 |
| DE | 19962317 | 12/1999 |
| DE | 20007908 | 12/2000 |

(Continued)

OTHER PUBLICATIONS

International Patent Application No. WO 00/66012, filed Nov. 9, 2000.

*Primary Examiner* — Sameh Boles
(74) *Attorney, Agent, or Firm* — Howard & Howard Attorneys PLLC

(57) ABSTRACT

An osteosynthesis plate is described, which is suitable for treating jaw fractures. The osteosynthesis plate has a plane of the plate as well as two plate sections 12, 14 with associated longitudinal axes 16, 18 extending substantially within the plane of the plate and inclined or staggered with respect to one another. Through openings 20, 22 inclined to the plane of the plate are formed in each of the two plate sections 12, 14. The angular alignments of the through openings 20, 22 within the plane of the plate differ with respect to a longitudinal axis 16 serving as reference line from one another by less than approximately 60°. In applications in the jaw region this slight deviation of the angular alignments permits an intraoral securement of the osteosynthesis plate. A transbuccal access through the cheek can thus be dispensed with.

15 Claims, 17 Drawing Sheets

(56) References Cited

FOREIGN PATENT DOCUMENTS

| | | |
|---|---|---|
| DE | 10140442 | 8/2001 |
| EP | 0290138 | 9/1988 |
| EP | 1034806 | 9/2000 |
| EP | 1153577 | 11/2001 |

\* cited by examiner

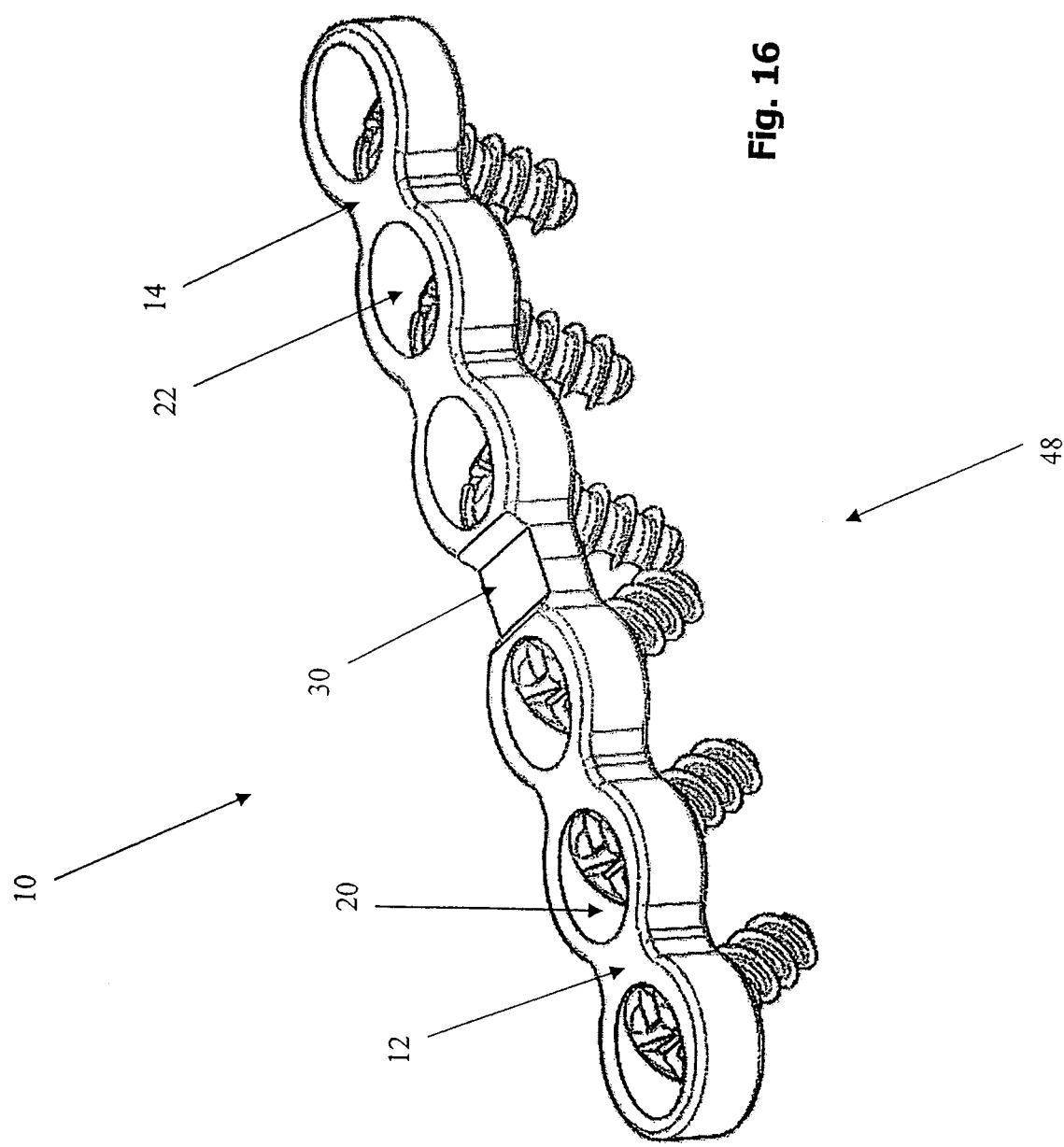

OSTEOSYNTHESIS PLATE COMPRISING THROUGH-OPENINGS WHICH ARE INCLINED IN RELATION TO THE PLANE OF THE PLATE

CROSS-REFERENCE TO RELATED APPLICATION

The instant application claims priority to and all the advantages of International Patent Application No. PCT/EP2006/006365, filed on Jun. 30, 2006, which claims priority to German Patent Application No. 10 2005 032 026.0, filed on Jul. 8, 2005, the entire specifications of both of which are expressly incorporated herein by reference.

FIELD OF THE INVENTION

The present invention relates to an osteosynthesis plate with through openings inclined relative to the plane of the plate. Such osteosynthesis plates can be used to treat fractures in the region of the head and in particular to treat jaw fractures.

BACKGROUND OF THE INVENTION

Osteosynthesis plates for the treatment of fractures have been known for more than 100 years. The most commonly used osteosynthesis plates have a linear (or elongated) shape and are provided with a plurality of through openings running perpendicular to the plane of the plate. In order to fix an osteosynthesis plate to a bone or bone fragment fastening elements (normally bone screws) are inserted through the through openings into the bone or bone fragment.

For individual cases it has proved convenient to form the through openings inclined relative to the plane of the plate. Often the provision of through openings inclined relative to the plane of the plate is connected with specific anatomical features or with special requirements, such as the generation of compression forces acting at specific angles.

In a linear osteosynthesis plate the alignment of through openings inclined relative to the plane of the plate can in principle be uniquely described by two angles $\alpha$ and $\beta$. This situation will now be described with reference to FIGS. 17 and 18.

As illustrated in FIG. 17, a first angle $\alpha$ denotes the inclination of a through opening O with respect to a line S perpendicular to the plane of the plate. The plane of the plate in FIG. 10 is inclined perpendicular to the plane of the drawing. A second angle $\beta$ denotes according to FIG. 18 an angular alignment of the through opening O within the plane of the plate with respect to a plate longitudinal axis L. The plane of the plate runs in FIG. 18 parallel to the plane of the drawing.

The angles $\alpha$ and $\beta$ provide an unambiguous angular characterisation by restricting the first angle $\alpha$ to the range from 0° to 90° and having the second angle $\beta$ run from 0° to 360°. In the following discussion all angles are given in the anticlockwise direction and relative to a directed reference line (for example relative to a plate longitudinal axis pointing in a specific direction).

In U.S. Pat. No. 5,588,674 in FIGS. 5 and 6 a linear osteosynthesis plate is illustrated, which comprises a total of four through openings inclined to the plane of the plate. Each of these four through openings intersects the plane of the plate approximately at an angle of inclination $\alpha$=45°. The inclined through opening 26b has an angular alignment $\beta$=0° with respect to a plate longitudinal axis pointing to the free end 21 of the osteosynthesis plate 20. The remaining three inclined through openings have an opposite angular alignment $\beta$=180°.

From DE 199 62 317 A1 a linear osteosynthesis plate is known with two through openings aligned perpendicular to the plane of the plate and two through openings inclined to the plane of the plate. In this osteosynthesis plate the two through openings inclined to the plane of the plate have in each case an angle of inclination $\alpha$ of approximately 65° with respect to a straight line perpendicular to the plane of the plate. The angular alignment within the plane of the plate is in the case of the first inclined through opening $\beta$=0° with respect to the plate longitudinal axis, and in the case of the second inclined through opening $\beta$=180°.

From Christian Krenkel, Biomechanics and Osteosynthesis of Condylar Neck Fractures of the Mandible, Quintessence Publishing Co., Inc. Carol Stream, Ill., 1994, pp. 56 to 60, further linear osteosynthesis plates are known, which are used to treat fractures of the lower jaw. Since for aesthetic reasons (in order to avoid facial scars) fractures in the region of the lower jaw should be treated by surgical intervention from underneath the jaw, the through openings of the osteosynthesis plates are formed inclined to the plane of the plate. In the proposed osteosynthesis plates the angle of inclination $\alpha$ is between 30° and 90°. The angular alignment $\beta$ of the through openings is either 0°, 45°, 90° or 135°.

The object of the invention is to provide an osteosynthesis plate for the treatment of fractures, in particular fractures in the region of the head such as lower jaw fractures, which can be fixed in a simple manner and with improved functionality to the bone.

SUMMARY OF THE INVENTION

This object is achieved by an osteosynthesis plate with a plane of the plate, with a linear first section with a first longitudinal axis and extending substantially within the plane of the plate, with a linear second section with a second longitudinal axis and extending substantially within the plane of the plate inclined or staggered with respect to the first section, with at least one first through opening in the first section, which is inclined to the plane of the plate and has with respect to the first longitudinal axis a first angular alignment within the plane of the plate, and at least one second through opening in a second section, which is inclined to the plane of the plate and has with respect to the first longitudinal axis of the first section a second angular alignment within the plane of the plate, wherein the first and second angular alignments with respect to the first longitudinal axis differ from one another by less than about 60°.

Although the osteosynthesis plate at least in the basic state or as-supplied state extends substantially within a general plane of the plate, this does not prevent the plate or individual sections of the plate from being bent outwards from the plane of the plate before or during use. Thus, it may be convenient to adapt the osteosynthesis plate before its securement to a bone and/or bone fragment, by bending it to match the specific anatomical features of the fracture region. This matching is as a rule carried out by the operating surgeon. It is however also possible for the osteosynthesis plate to be bent outwards to some extent from the general plane of the plate already in the as-supplied state, so as to match anatomical features. Such osteosynthesis plates are included in the scope of protection of the invention.

The angular alignments of the first through opening and of the second through opening with respect to the first longitudinal axis serving as reference axis may be identical or different. Often angular alignments differing somewhat from one another by more than 0° or more than 10° (up to about 60° or up to about 45°) with respect to the first longitudinal axis are suitable for purposes of manipulation. It is also possible for the first angular alignment to be inclined to the first longitudinal axis and/or for the second angular alignment to be inclined to the second longitudinal axis. This means in the diagram in FIG. 18 that the angle β is chosen to be different from 0° and also different from 180°. Thus, the angle β can be chosen to be between approximately 10° and 170°, or between approximately 190° and 350°.

The angles of the first through opening and of the second through opening inclined to the plane of the plate (i.e. the angle of inclination α in the diagram of FIG. 17) can be chosen to be identical or different. The first through opening can intersect the plane of the plate at an angle of inclination of approximately 20° to 80°. Also, an angle of inclination within the range from approximately 30° to 70° is also feasible. The angle of inclination at which the second through opening intersects the plane of the plate can likewise vary in these angular ranges from approximately 20° to 80° or from approximately 30° to 70°.

According to a first variant the first angular alignment to the first longitudinal axis is between approximately +90° and −90°, between approximately +60° and −60° or between approximately +40° and −40° (for example with respect to a direction facing away from the second section or facing towards a free end of the first section). According to a second variant, which can be combined with the first variant, the second angular alignment with respect to the second longitudinal axis is between approximately 60° and 180° or between approximately 70° and 130° (for example with respect to a direction facing away from the first section or a direction facing towards a free end of the second section). According to a third variant, which can be combined with the first variant, the second angular alignment to the second longitudinal axis is between approximately 180° and 300° or between approximately 220° and 290° (for example with respect to a direction facing away from the first section or a direction facing towards a free end of the second section). The second variant and the third variant can be used for osteosynthesis plates for different halves of the body (right/left).

The first section and the second section can directly adjoin one another or can be connected to one another by one or more connecting sections. The connecting sections can have a linear or bent shape.

In the case of a second section inclined to the first section, the angle between the first section and the second section can be between approximately 90° to 160° and in particular between approximately 110° to 150°. The first section and the second section (or their longitudinal axes) can also run parallel and staggered with respect to one another. In this case at least one connecting section is provided between the first section and the second section. The at least one connecting section can extend inclined or perpendicular to the first and second section.

In order to enable a surgeon to carry out more easily the already mentioned matching of the osteosynthesis plate to the relevant anatomical features, the osteosynthesis plate can comprise at least one bending region of reduced plate thickness and/or reduced plate width and/or of meandering shape. According to a first variant the bending region (for example as connecting section) is formed at the transition between the first section and the second section. According to a second variant, which can be combined with this first variant, the bending region is provided between two adjacent through openings.

The osteosynthesis plate is dimensioned depending on the surgical situation in each case. In particular, in cases involving the lower jaw region the first section of the osteosynthesis plate can have a length between approximately 3 and 100 mm (for example between 5 and 60 mm and preferably between 6 and 25 mm) and the second section can have a length between approximately 3 and 100 mm (for example between 5 and 60 mm and preferably between 6 and 25 mm). The overall length of the plate can vary between 6 and 200 mm.

The osteosynthesis plate can in the region of the first section and/or in the region of the second section have a maximum plate thickness between approximately 0.5 and 3.5 mm. In one possible configuration the plate thickness is chosen so that a head of a fastening element (in any case most of it) can be sunk or embedded in the plate. In order to support the embedding of the head, the at least one first through opening and/or the at least one second through opening can include underneath a plate surface a stop means for the head of the fastening element.

In order to provide a reliable securement of the osteosynthesis plate, a plurality (for example at least 2 to approximately 5) first through openings and a plurality (for example at least 2 to approximately 5) second through openings are provided. In this connection the mutual interspacing of the first through openings can be different from the mutual interspacing of the second through openings. This arrangement is particularly convenient if the length of the first section differs from the length of the second section. The through openings can have a diameter of approximately 1.5 to 3.5 mm, preferably approximately 2 to 3 mm.

BRIEF DESCRIPTION OF THE DRAWINGS

Further implementations and advantages of the invention follow from the following description of preferred embodiments and from the figures, in which:

FIG. 16 shows in the linear base state a further osteosynthesis plate, in particular for treating jaw fractures;

DESCRIPTION OF PREFERRED EMBODIMENTS

Figure 1:
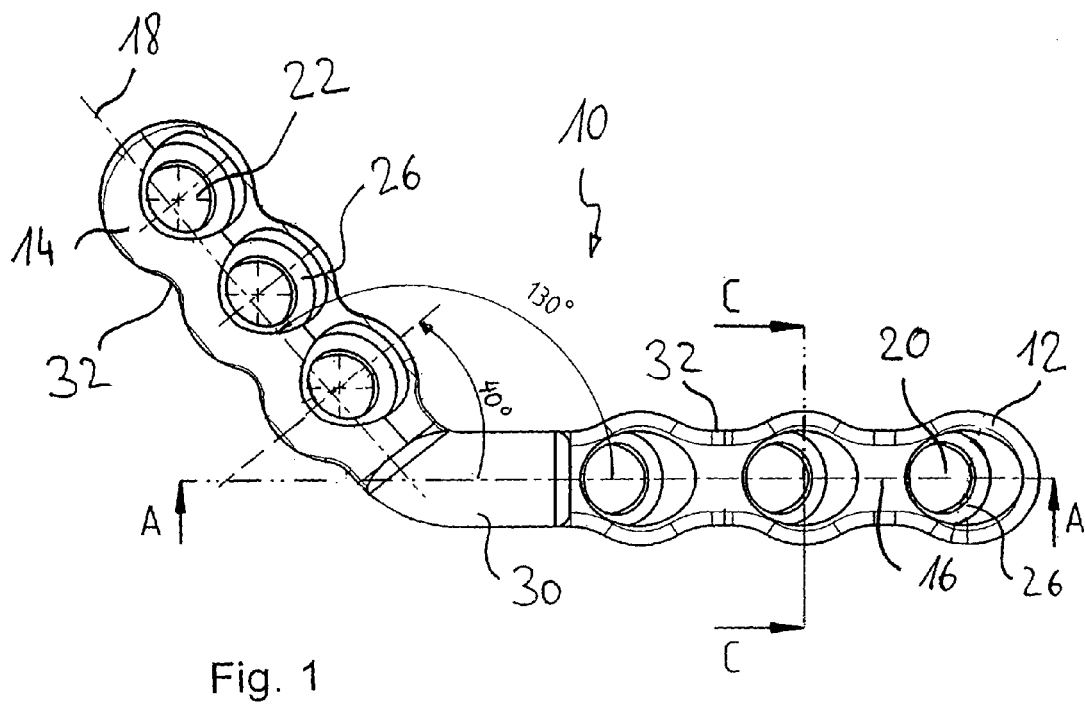
FIGS. 1 and 2 each show a plan view of a first embodiment of an osteosynthesis plate.

The osteosynthesis plate according to the invention is discussed hereinafter with the aid of several embodiments. Identical and corresponding elements are identified here by the same reference numeral.

Figure 2:
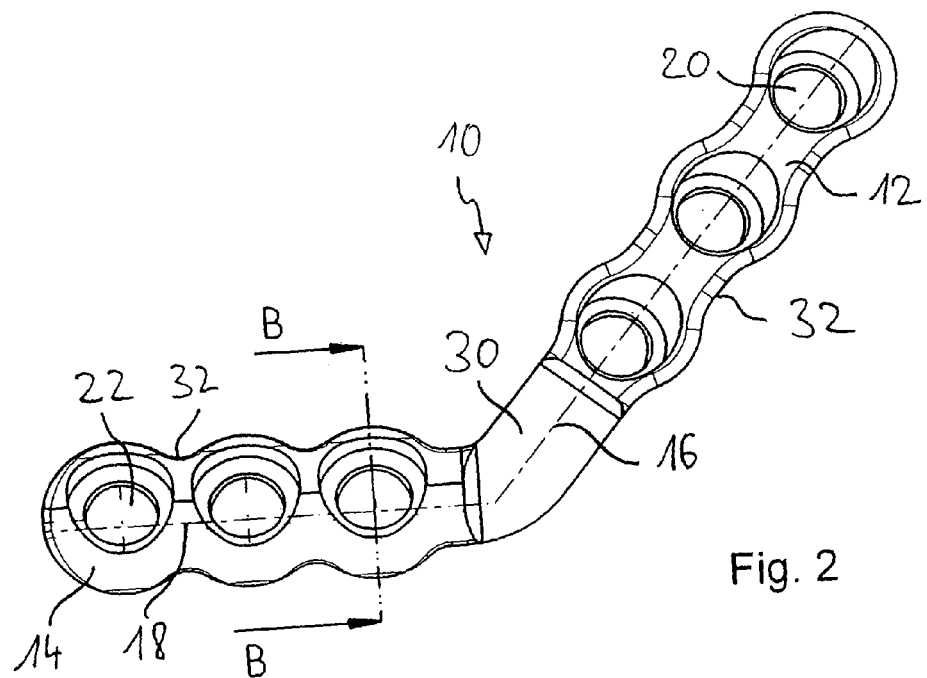

FIGS. 1 and 2 show in each case a plan view of a first embodiment of an osteosynthesis plate 10 in different alignments. FIGS. 3 to 7 and FIGS. 8A and 8B show further views of this osteosynthesis plate 10.

The osteosynthesis plate 10 consists of titanium and is suitable in particular for treating jaw fractures (in particular fractures in the region of the mandibular angle). The osteosynthesis plate 10 illustrated in FIGS. 1 to 7, 8A and 8B is a plate for the right-hand mandibular angle. The plate illustrated in FIG. 9 is intended for the left-hand mandibular angle. The left-hand osteosynthesis plate of FIG. 9 is the mirror image counterpart of the right-hand osteosynthesis plate 10. For this reason the description of the right-hand osteosynthesis plate 10 applies, apart from a few exceptions, also to the left-hand osteosynthesis plate according to FIG. 9. The exceptions will be discussed in more detail in connection with the description of FIG. 9.

The osteosynthesis plate 10 according to the first embodiment extends in the as-supplied state within a general plane of the plate, which in FIGS. 1 and 2 runs parallel to the plane of the drawing. The osteosynthesis plate 10 has two adjoining linear plate sections 12, 14 with associated longitudinal axes 16, 18. The two plate sections 12, 14 run inclined to one another within the plane of the plate. As can be seen from FIG. 1, the angle of intersection between the longitudinal axes 14, 16 of the two plate sections 12, 14 is approximately 130° in the illustrated embodiment. The length of the plane section 12 (measured from the point of intersection of the two longitudinal axes 16, 18 up to the free end of the section 12) is approximately 14 mm, and the length of the plate section 14 (measured from the point of intersection of the two longitudinal axes 16, 18 up to the free end of the section 14) is approximately 10 mm.

Three identically shaped through openings 20 are formed in the plate section 12, and three likewise identically shaped through openings 22 are formed in the plate section 14. The through openings 20, 22 have a diameter of 2.4 mm in the narrowest region.

Figure 17:
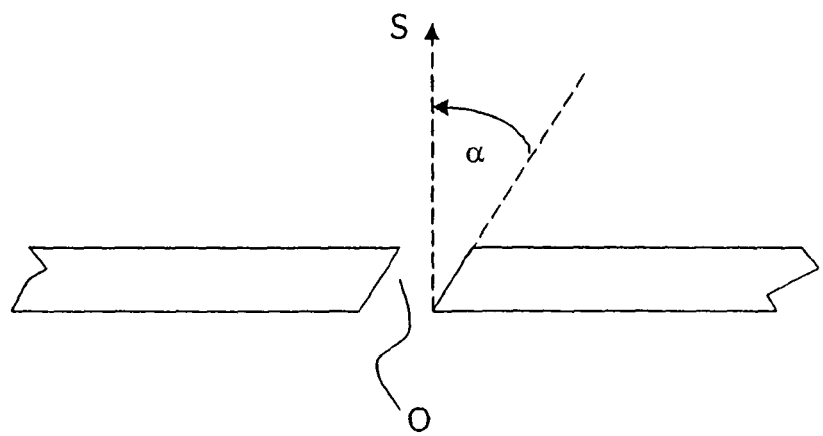
FIG. 17 is a diagrammatic representation of the angle of inclination α between a through opening inclined relative to the plane of the plate, and the plane of the plate itself.

The through openings 20 in the plate section 12 intersect the plane of the plate at an angle of inclination α=60°. This situation can be seen in FIG. 3, which shows a section along the line A-A of FIG. 1. The through openings 22 of the plate section 14 intersect the plane of the plate similarly at an angle of inclination of alpha=60°. This can be seen in FIG. 4, which shows a section along the line B-B of FIG. 2. As regards the definition of the angle α, reference should be made to FIG. 17.

Figure 18:
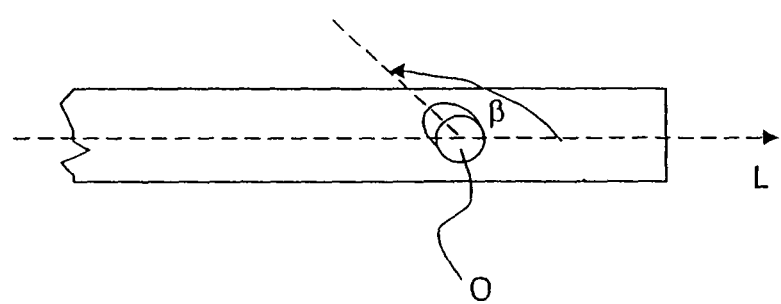
FIG. 18 is a diagrammatic representation of the angular alignment β within the plane of the plate for a through opening inclined relative to the plane of the plate.

The through openings 20 of the plate section 12 have within the plane of the plate an angular alignment of β=0° with respect to the longitudinal axis 16. The angular alignment with respect to the longitudinal axis 16 is determined in the direction of a free end of the plate section 12. The through openings 22 of the plate section 14 have within the plane of the plate an angular alignment of β=270° with respect to the longitudinal axis 18 (and in the direction of the free end of the plate section 14). The through openings 22 have an angular alignment β=40° with respect to the longitudinal axis 16 of the plate section 12 (again referred to the direction of the free end of the plate section 12). The angular alignment of β=40° of the through openings 22 of the plate section 14 with respect to the longitudinal axis 16 of the plate section 12 is shown in FIG. 1. As regards the determination of the angle β, reference should be made to FIG. 18.

In the osteosynthesis plate 10 according to FIGS. 1 to 7, 8A and 8B the through openings 20 consequently have an angular alignment in the plane of the plate of β=0° and the through openings 22 have an angular alignment in the plane of the plate of β=40° (in each case referred to the longitudinal axis 16 of the plate section 12). The difference in the angular alignments of the through openings 20 and of the through openings 22 within the plane of the plate is therefore approximately 40°.

Figure 3:
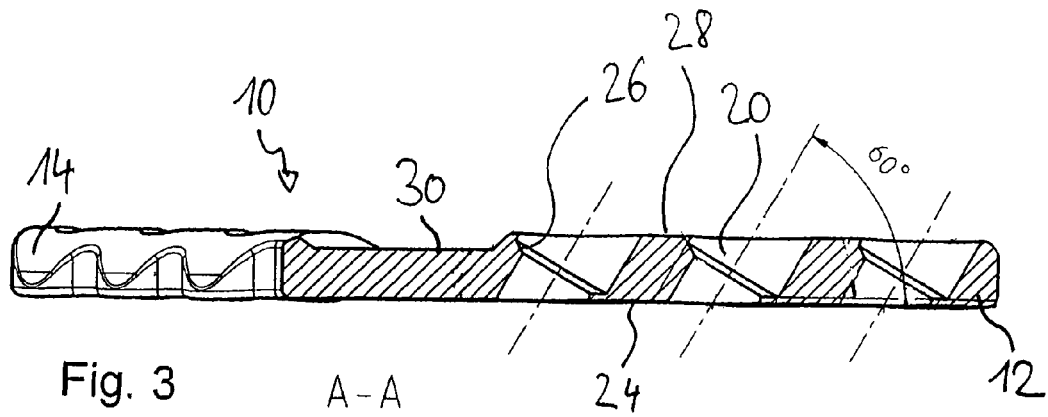
FIG. 3 is a section along the line A-A in FIG. 1.
Figures 4, 5:
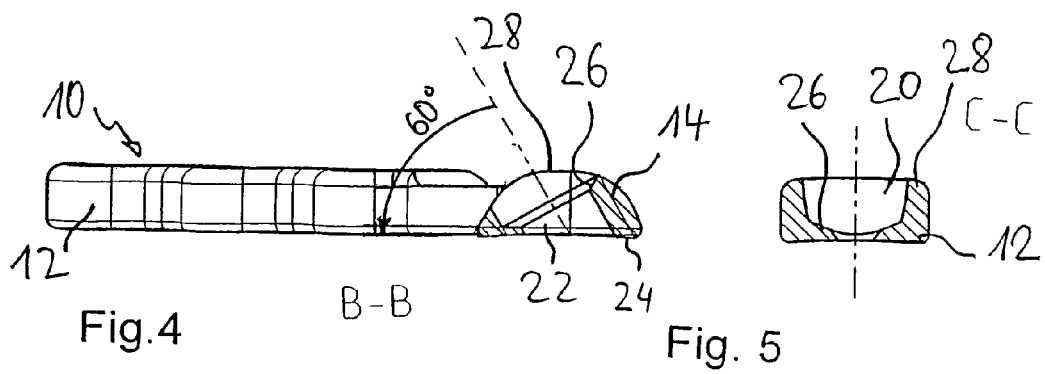
FIG. 4 is a section along the line B-B in FIG. 2.
FIG. 5 is a section along the line C-C in FIG. 1.
Figure 6:
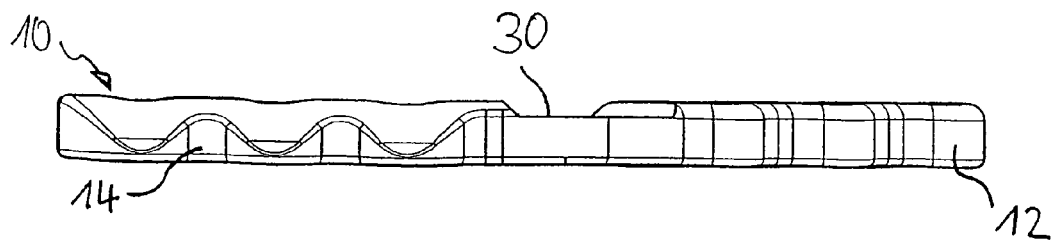
FIG. 6 is a side view of the osteosynthesis plate of the first embodiment.
Figure 7:
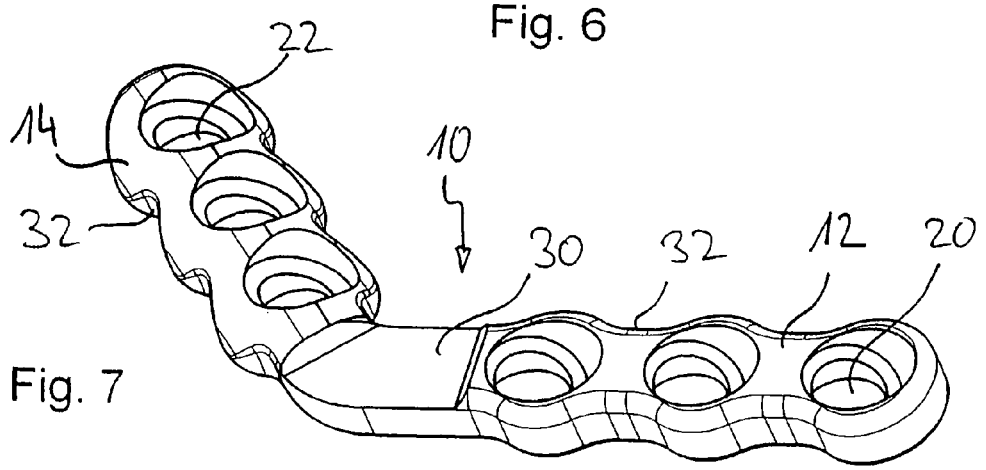
FIG. 7 is a perspective view of the osteosynthesis plate of the first embodiment.

As can readily be recognised especially in FIGS. 3 and 4, the through openings 20 in the plate section 12 (just as the through openings 22 in the plate section 14) have an internal diameter that reduces in a step-wise manner in the direction of the lower side of the plate 24. In this way a bearing surface 26 acting as a stop means for the head of a securement element is formed in each case within the through openings 20, 22. The bearing surface 26 is formed underneath the plate surface 28 and above the lower side of the plate 24. Since in any case the lowest region of the bearing surface 26 (cf. FIG. 5) lies underneath the plate surface 28, the head of a securement element inserted into the through openings 20, 22 can be sunk at least partly in the osteosynthesis plate 10.

Figure 8A:
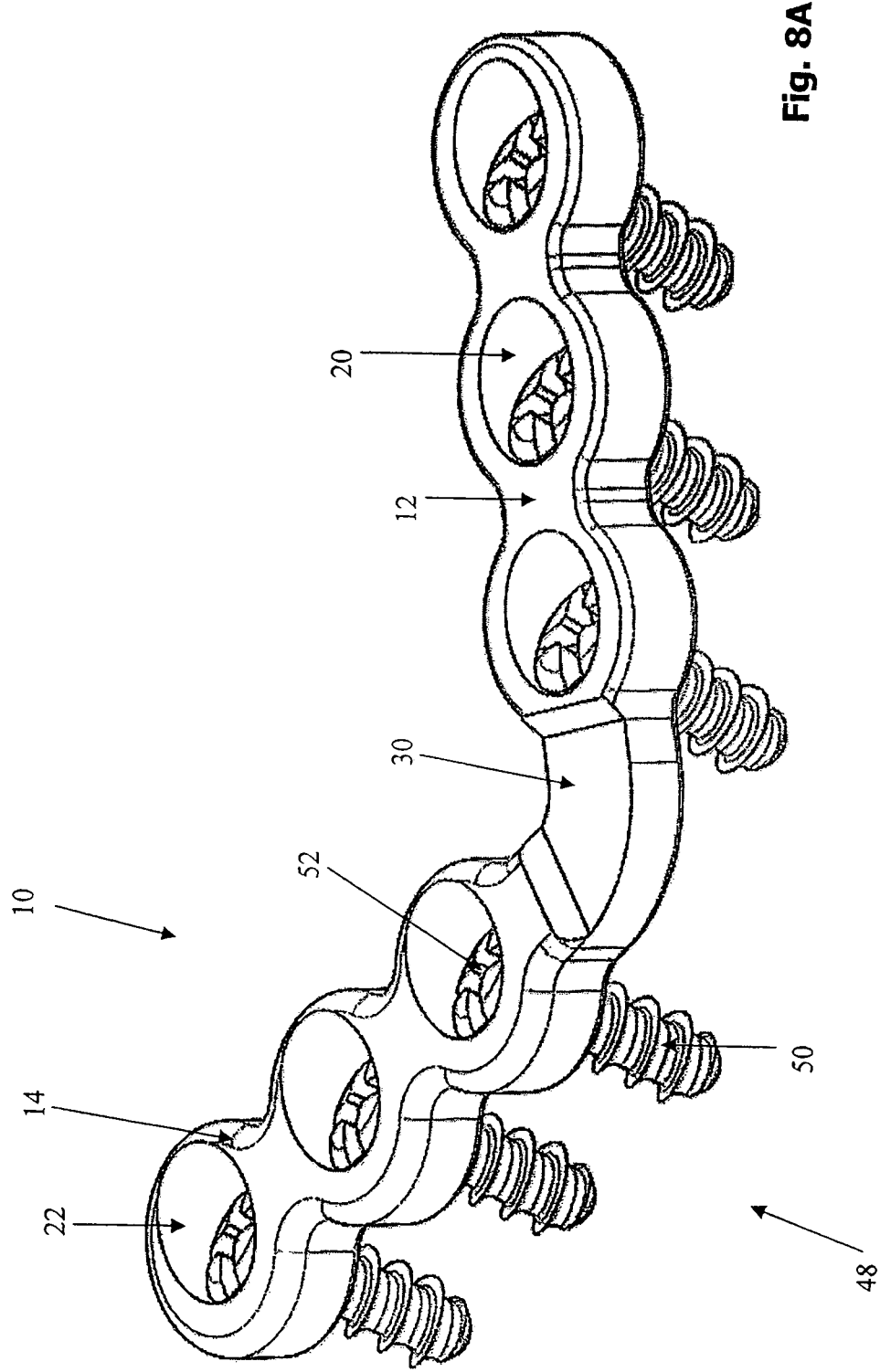
FIGS. 8A and 8B each show a perspective view of the osteosynthesis plate of the first embodiment with bone screws accommodated in through openings.
Figure 9:
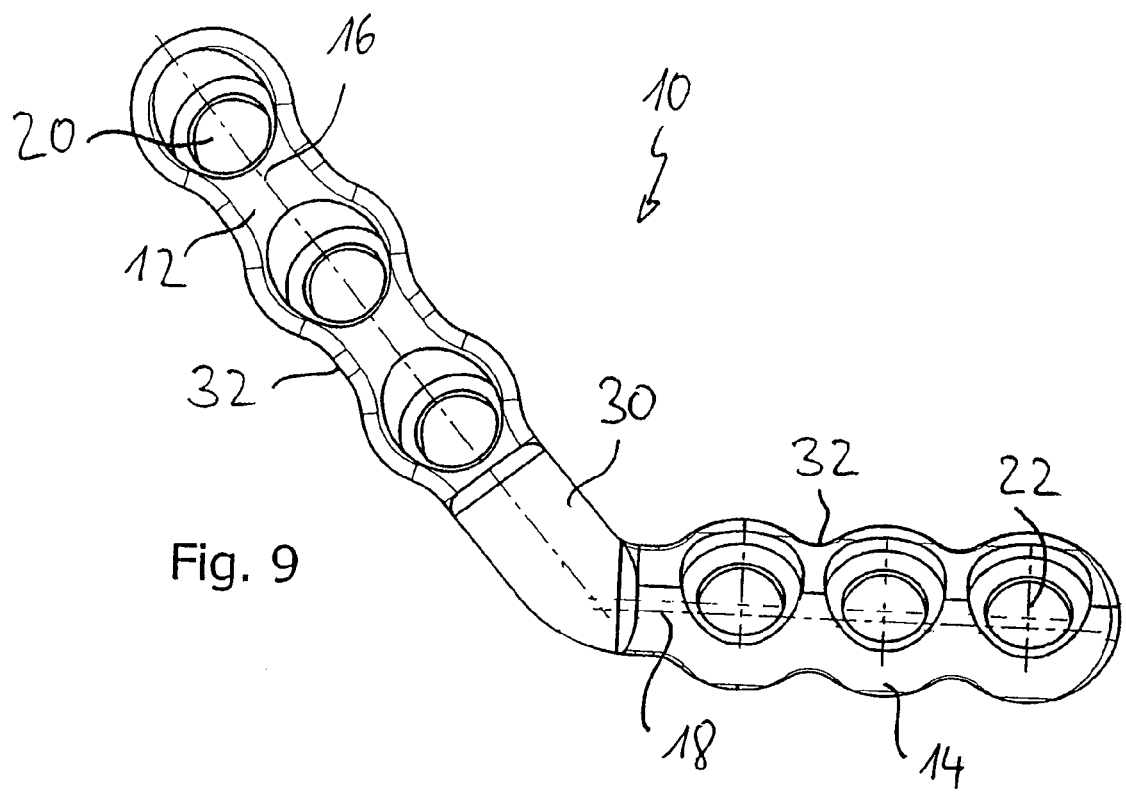
FIG. 9 is a view of a second embodiment of an osteosynthesis plate.

In FIG. 8A it can clearly be seen that the shanks 50 of bone screws 48 in the plate section 12 run up to the different angular alignment (Δβ=40°) substantially parallel to the shanks 50 of bone screws 48 in the plate section 14. Furthermore, it can readily be seen in the illustration according to FIG. 8A that the heads 52 of the bone screws 48 are accommodated sunk relative to the upper side of the plate.

Figure 8B:
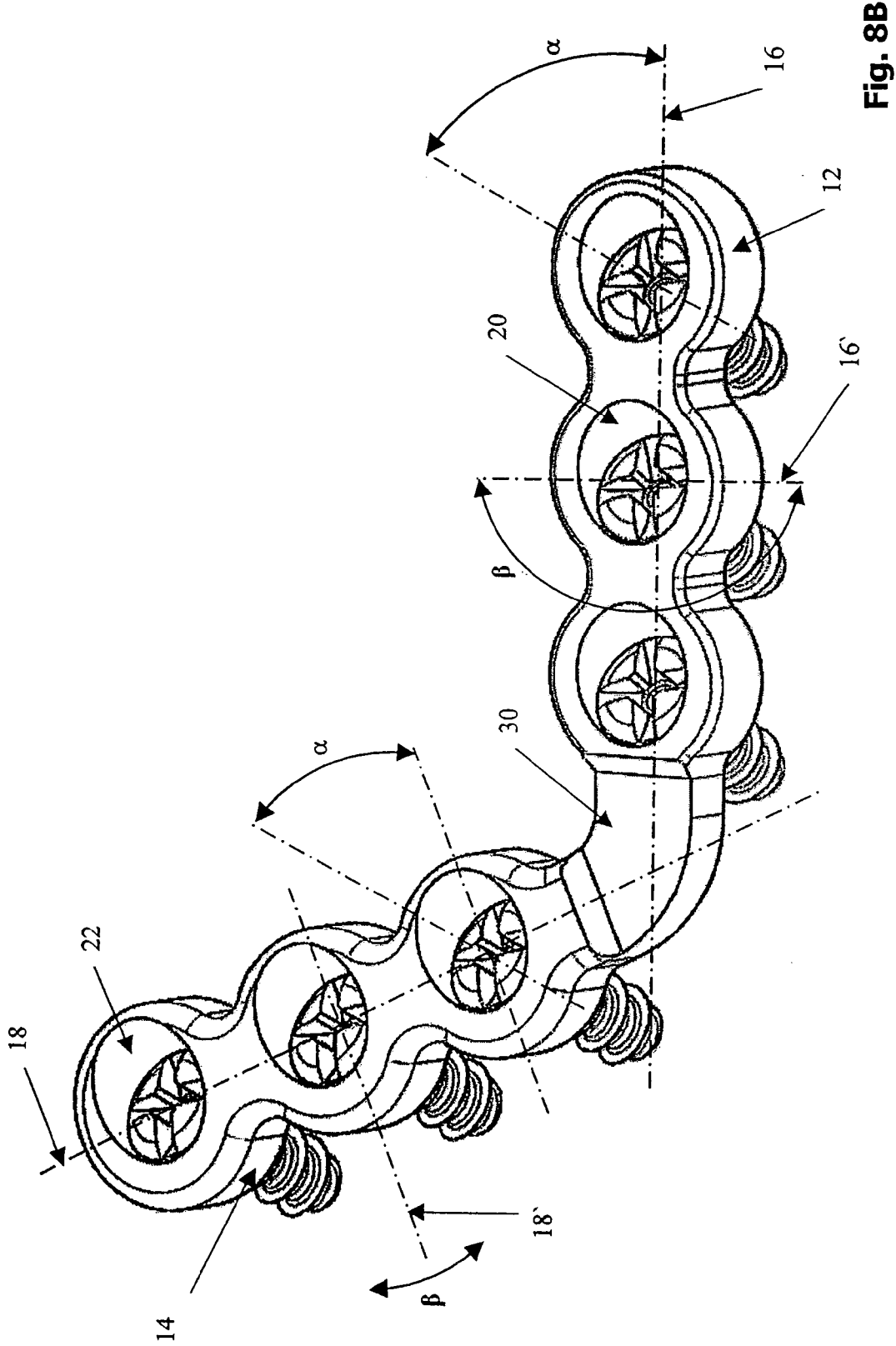

With respect to FIG. 8B it should also be mentioned that the auxiliary lines 16', 18' shown there and running perpendicular to the longitudinal axes 14, 16 serve to illustrate the angular alignment region β. As shown in FIG. 8B, the angular alignment β with respect to the auxiliary lines 16', 18' can vary by ±90°, preferably by approximately 60°.

The planar osteosynthesis plate 10 in the as-supplied state has a plurality of bending regions of reduced plate thickness or reduced plate width. These bending regions enable the surgeon to adapt and match the osteosynthesis plate 10 to the anatomical features in the fracture region. In this connection the osteosynthesis plate 10 can by means of suitable tools such as bending forceps be bent within the plane of the plate as well as outwardly from the plane of the plate.

A first bending region 30 of the osteosynthesis plate 10 is according to FIG. 1 arranged at the transition between the plate section 12 and the plate section 14. As can be seen from the side view according to FIG. 6, the osteosynthesis plate 10 has in the bending region 30 a minimal width and a lower height than in regions outside the bending region 30. This step-wise reduction of the plate thickness (from a maximum ca. 2 mm outside the bending region 30 to ca. 1.5 mm in the bending region 30) and of the plate width facilitates the bending of the osteosynthesis plate 10 by the surgeon.

A plurality of second bending regions 32 are according to FIG. 1 formed in each case between two adjacent through openings 20 of the plate section 12 and also between two adjacent through openings 22 of the plate section 14. These further bending regions 32 are formed by regions of reduced plate width.

FIG. 9 shows the left-hand osteosynthesis plate 10 of a plate system, which also includes the right-hand osteosynthesis plate described above with reference to FIGS. 1 to 7, 8A and 8B. As already mentioned, the left-hand osteosynthesis plate 10 is the mirror symmetrical counterpart to the right-hand osteosynthesis plate. Accordingly the basic difference compared to the right-hand osteosynthesis plate is that the through openings 22 of the plate section 14 have a different angular alignment within the plane of the plate. Whereas in the right-hand plate the corresponding angular alignment β=270°, the through openings 22 of the left-hand osteosynthesis plate 10 have with respect to the longitudinal axis 18 and in the direction of the free end of the plate section 14, a mirror image-forming angular alignment β=90°. The difference in the angular alignments of the through openings 22 of the plate section 14 and of the through openings 20 of the plate section 12 (in each case referred to the longitudinal axis 16) is a constant 40°.

Figure 10:
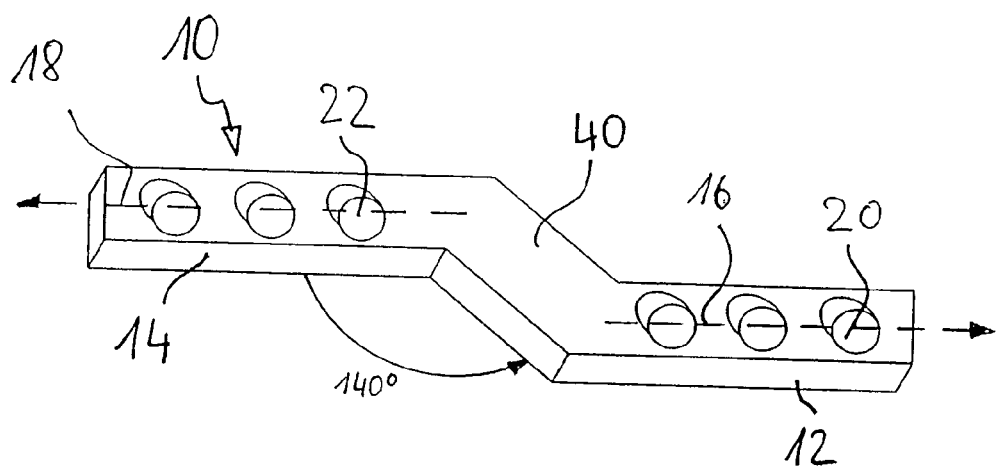
FIG. 10 is a perspective view of a third embodiment of an osteosynthesis plate.

FIG. 10 shows a further embodiment of an osteosynthesis plate 10 for treating fractures in the jaw region. The osteosynthesis plate 10 has two plate sections 12, 14, which are arranged parallel and staggered with respect to one another. Between the two plate sections 12, 14 is provided a connecting section 40, running inclined to each of these sections 12, 14. The connecting section 40 intersects the two plate sections 12, 14 at an angle of in each case approximately 140°.

Three identical through openings 20, 22 are formed in each case in each of the two plate sections 12, 14. The through openings 20, 22 intersect the plane of the plate at an angle of inclination α=45°. With respect to the longitudinal axis 16 of the plate section 12 and in the direction of the free end of the plate section 12 the angular alignment β of the through openings 20 within the plane of the plate is β=135°. The angular alignment β of the through openings 22 with respect to the longitudinal axis 18 of the plate section 14 and in the direction of the free end of the plate section 14 is β=45°. Referred to the longitudinal axis 16 of the plate section 12 and the free end of the plate section 12, the angular alignment β of the through openings 22 of the plate section 14 is β=135°. The angular alignments of the through openings 20 and of the through openings 22 therefore coincide with respect to the longitudinal axis 16 of the plate section 12.

Figure 11A:
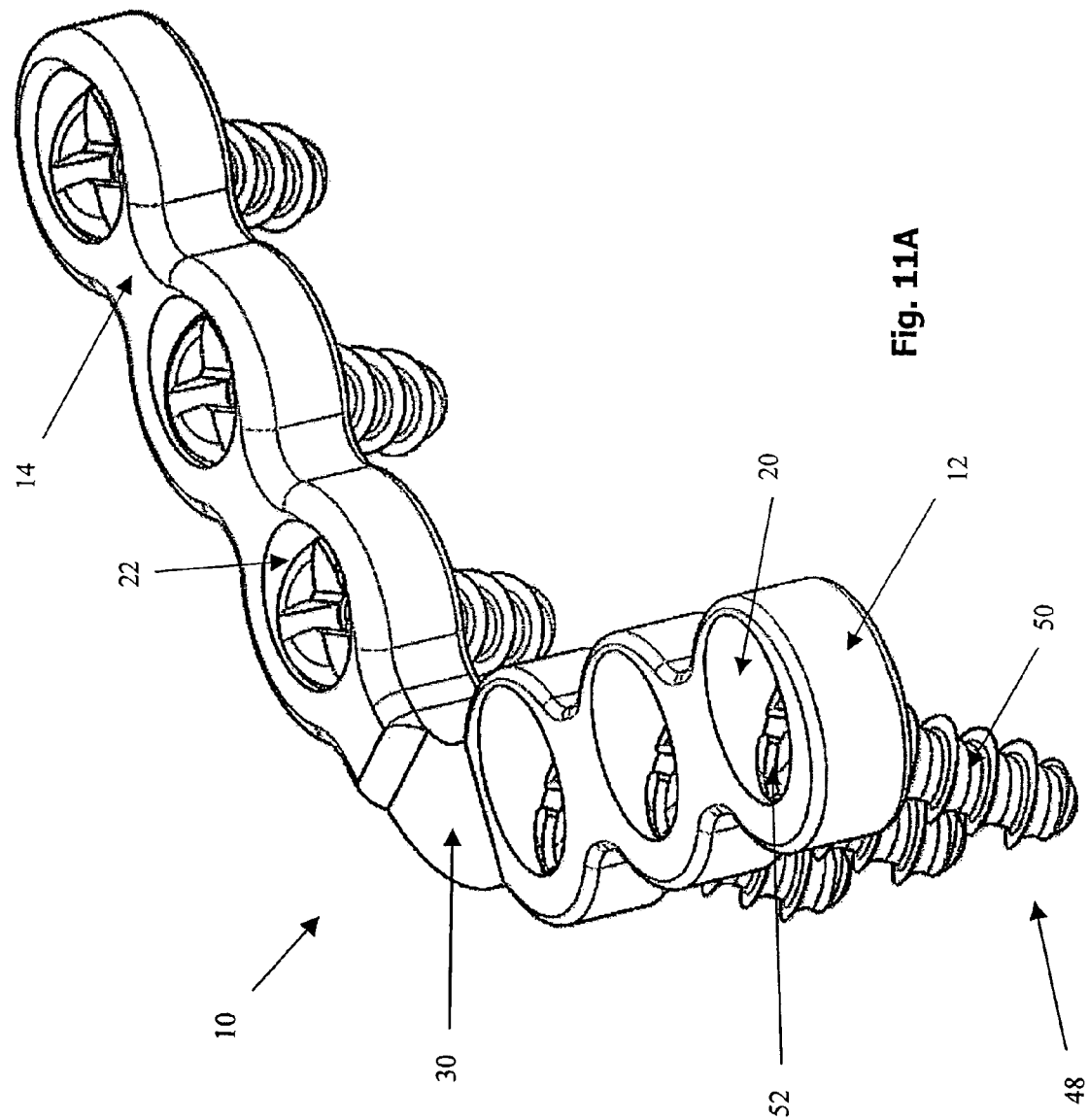
FIGS. 11A and 11B each show a perspective view of a fourth embodiment of an osteosynthesis plate with bone screws accommodated in through openings.
Figure 11B:
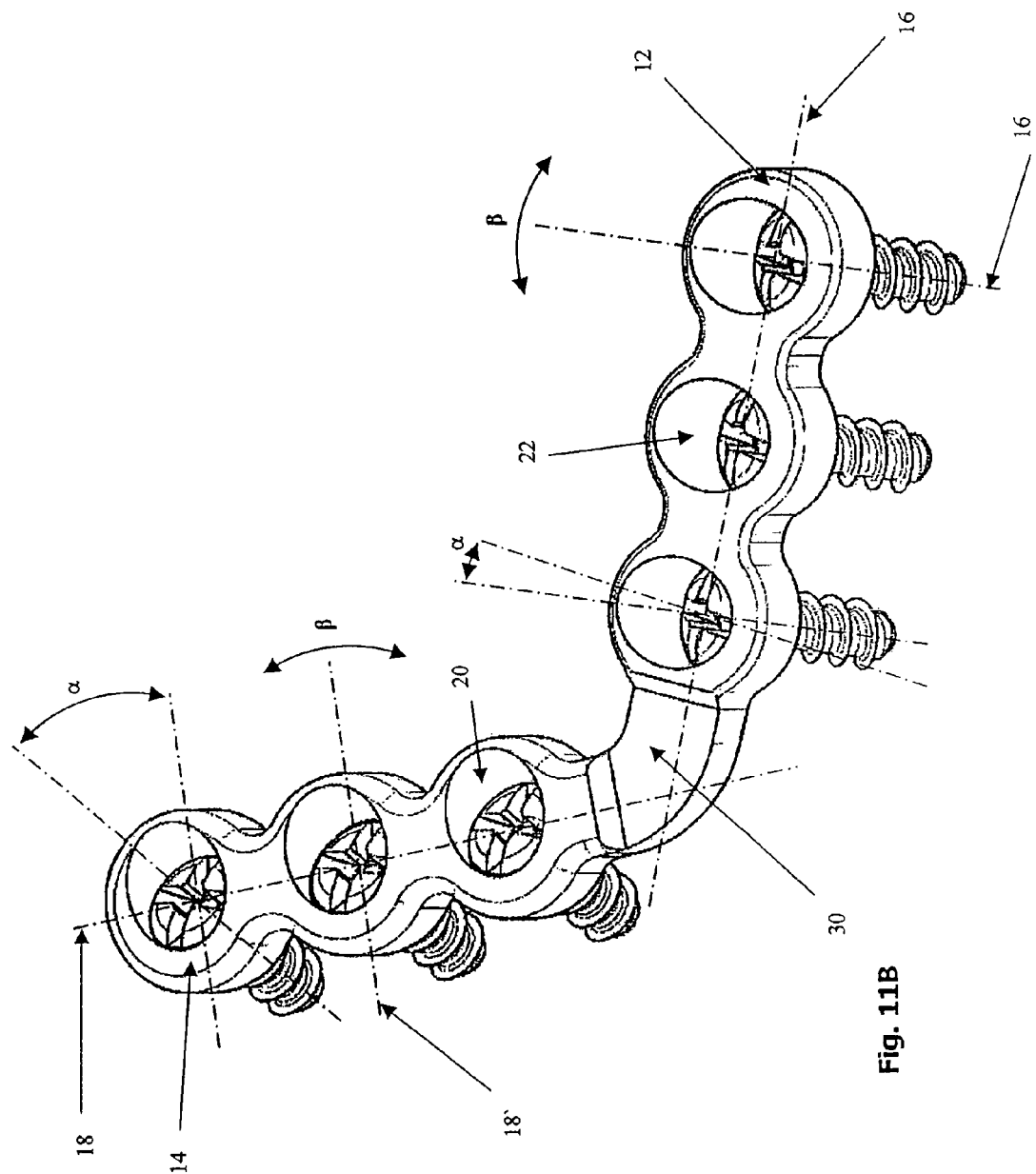

A further embodiment of an osteosynthesis plate 10 for treating fractures of the mandibular angle is illustrated in FIGS. 11A and 11B. The illustrated osteosynthesis plate 10 is substantially identical to the osteosynthesis plate 10 discussed with reference to FIGS. 1 to 7, 8A and 8B, except as regards the angular alignments of the through openings. For this reason only the differences will be discussed hereinafter.

A further embodiment of an osteosynthesis plate 10 is illustrated in FIGS. 11A and 11B. In this embodiment the two plate sections 12, 14 again enclose an angle of 130°. The through openings 20, 22 have in each case an angle of inclination α=60° with respect to the plane of the plate. The angular alignment of the through openings 20 of the plate section 12 within the plane of the plate (and referred to the free end of the plate section 12) is in this embodiment 90°. As in the first embodiment, the through openings 22 of the plate section 14 within the plane of the plate have with respect to the longitudinal axis 18 (and in the direction of the free end of the plate section 14) an angular alignment of β=270°. The difference of the angular alignments of the through openings 20 and of the through openings 22 within the plane of the plate is approximately 50°. The angular alignments of the through openings 20 and 22 can vary from the specified angular alignments by ±90°, preferably by approximately ±60°.

Figure 12A:
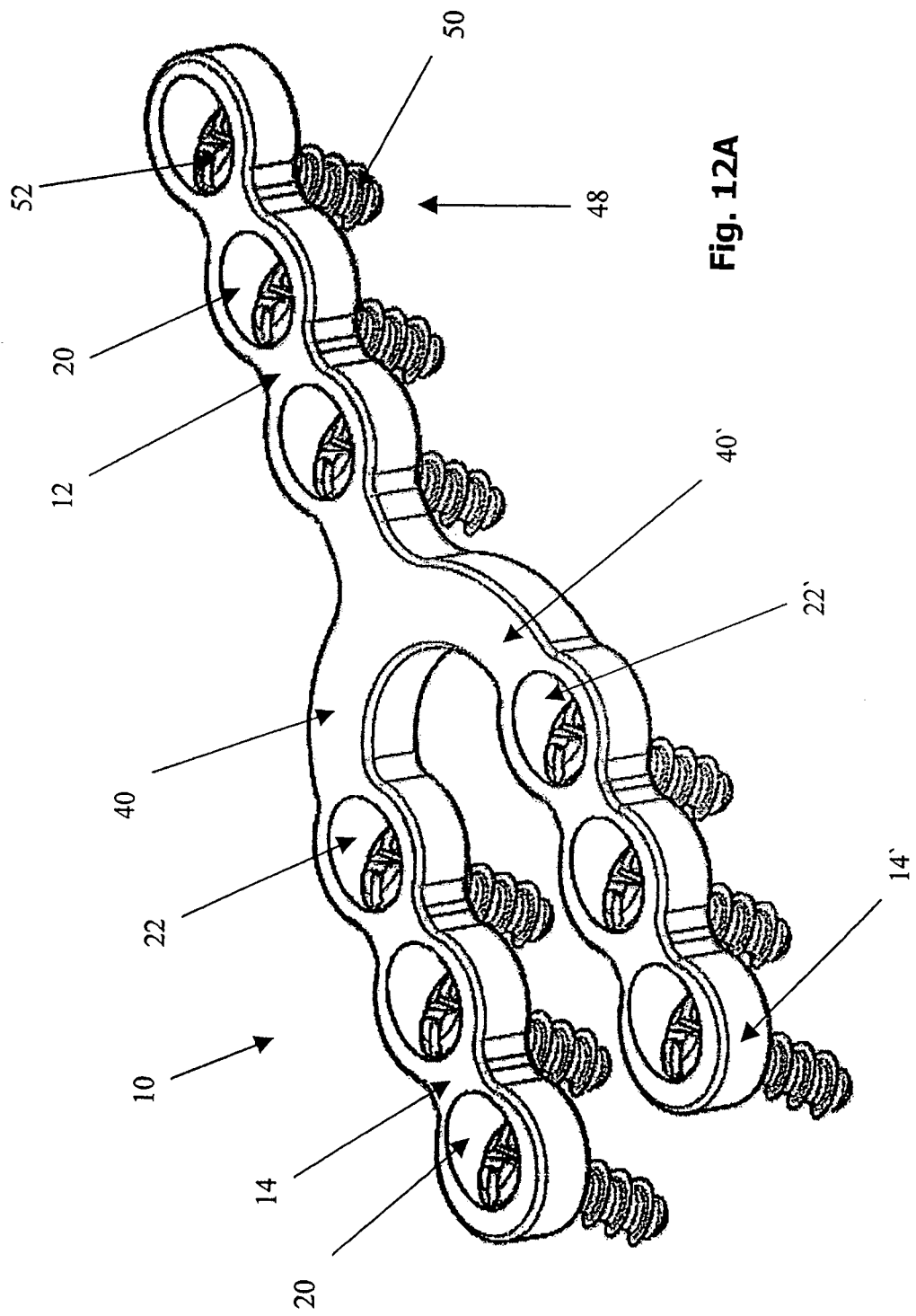
FIGS. 12A and 12B each show a perspective view of a fifth embodiment of an osteosynthesis plate with bone screws accommodated in through openings.
Figure 12B:
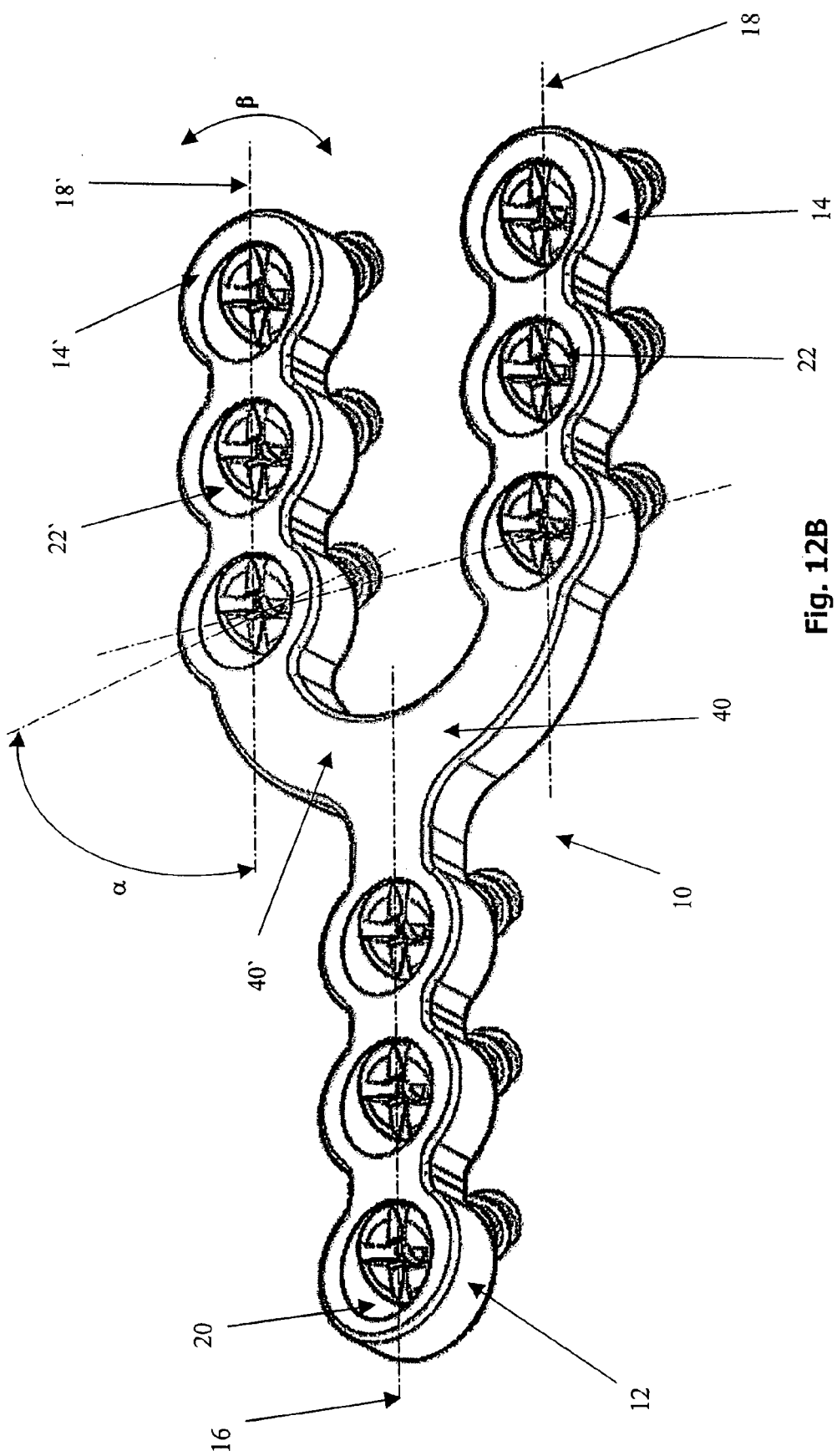

A further embodiment of an osteosynthesis plate 10 is illustrated in FIGS. 12A and 12B, with a total of three plate sections 12, 14, 14' and a total length of approximately 40 mm. The osteosynthesis plate 10 has a substantially fork-shaped configuration. The two plate sections 14, 14' run parallel and staggered with respect to the longitudinal axis 16 of the section 12. The plate section 12 is connected to the plate sections 14, 14' by a connecting section 40, 40' bent in each case in the shape of a quarter circle.

The fork-shaped configuration of the osteosynthesis plate 10 is determined by the fact that the two plate sections 14, 14' accommodate a nerve between them (for example in the region of the lower jaw). In this way damage to the nerve due to the bone screw 48 can be avoided.

The through openings 20 of the plate section 12 of the osteosynthesis plate 10 and also the through openings 20, 20' of the plate sections 14, 14' intersect the plane of the plate in each case at an angle of inclination α=60°. The through openings 20 of the plate section 12 have within the plane of the plate an angular alignment β=0° with respect to the longitudinal axis 16 and in the direction of a free end of the plate section 12. The through openings 22, 22' of the plate sections 14, 14' have within the plane of the plate an angular alignment β=180° relative to the respective longitudinal axis 18, 18' (and in the direction of the respective free end of the plate section 14, 14'. The through openings 22, 22' have an angular alignment β=0° with respect to the longitudinal axis 16 of the plate section 12 (again referred to the direction of the free end of the plate section 12). The difference in the angular alignments of the through openings 20 and of the through openings 22, 22' within the plane of the plate is therefore 0°.

Figure 13A:
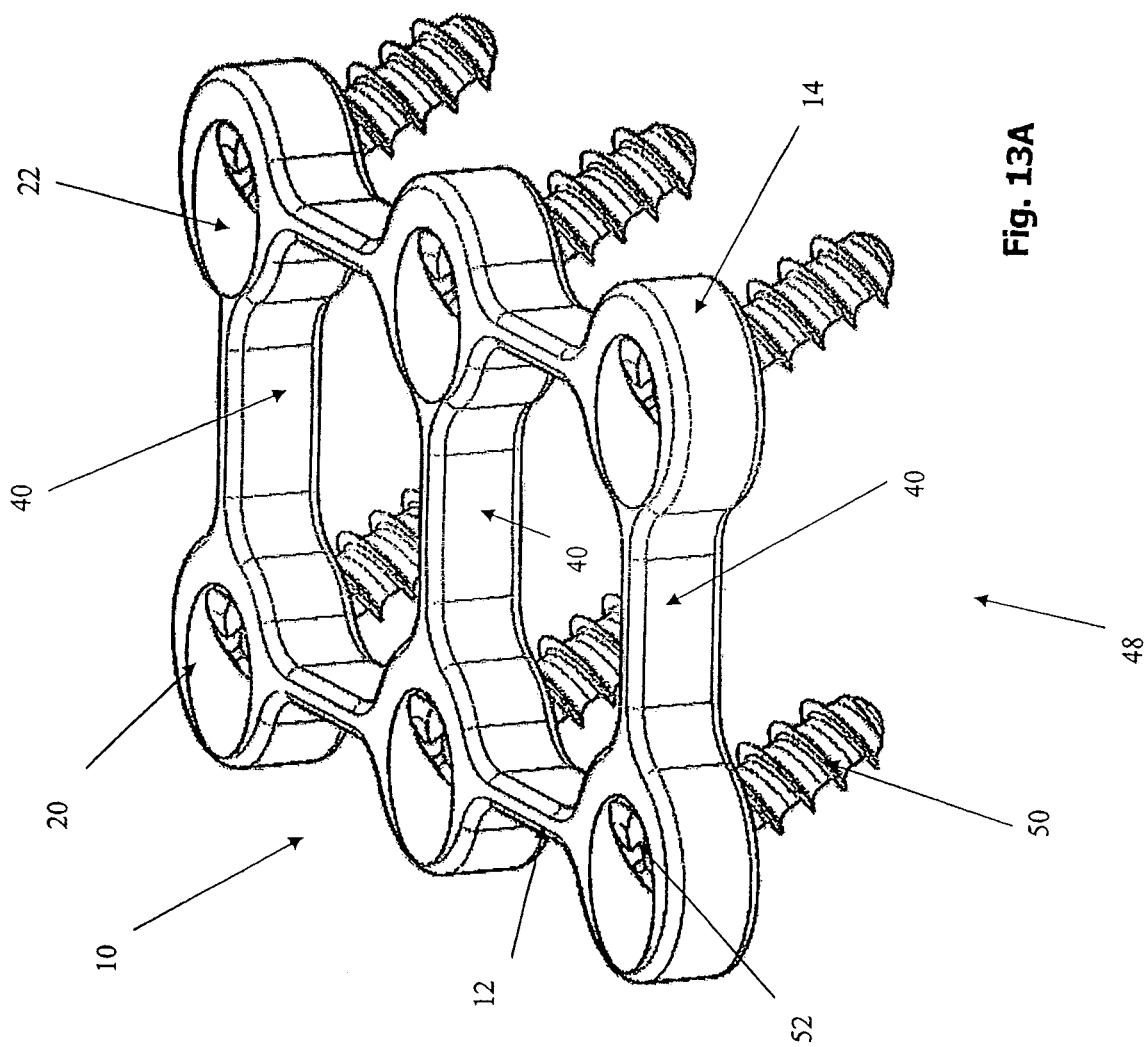
FIGS. 13A and 13B each show a perspective view of a sixth embodiment of an osteosynthesis plate with bone screws accommodated in through openings.
Figure 13B:
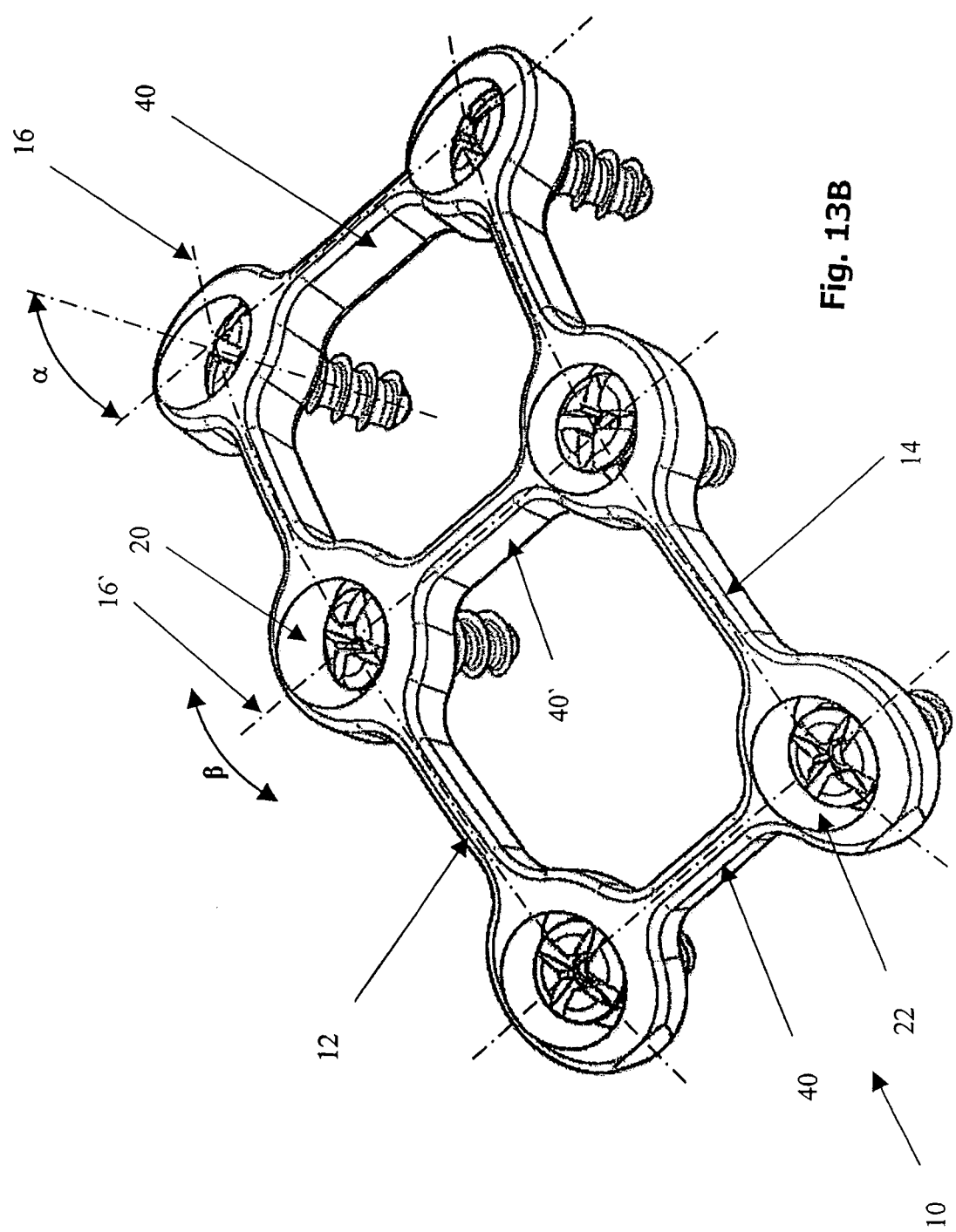

A further embodiment of an osteosynthesis plate 10 is illustrated in FIGS. 13A and 13B. The osteosynthesis plate 10 illustrated there has a substantially grid-shaped configuration with two plate sections 12, 14 running parallel and staggered with respect to one another. The plate sections 12, 14 are joined to one another in the region of oppositely located through openings 20, 22 by in each case a connecting section 40. In the example illustrated in FIGS. 13A and 13B, with two times three through openings 20, 22 (i.e. three per plate section 12, 14), three connecting sections 40 are therefore provided. The connecting sections 40 run parallel to one another and in this example intersect the plate section 12, 14 at a right angle. A modification of the osteosynthesis plate 10 illustrated in FIGS. 13A and 13B could have, instead of two times three through openings, two times four or three times four through openings.

The through openings 20, 22 of the osteosynthesis plate 10 of FIGS. 13A and 13B intersect the plane of the plate in each case at an angle of inclination α=60°. The through openings 20 of the plate section 12 have within the plane of the plate an angular alignment β=90°/270° with respect to a longitudinal axis of the plate section 12 (in the example of FIGS. 13A and 13B there is no preferred direction). The through openings 22 of the plate section 14 have the same angle of alignment β=90°/270° with respect to a longitudinal axis of the plate section 14. Accordingly the difference in the angular alignments of the through openings 20 and of the through openings 22 within the plane of the plate is 0°.

Figure 14A:
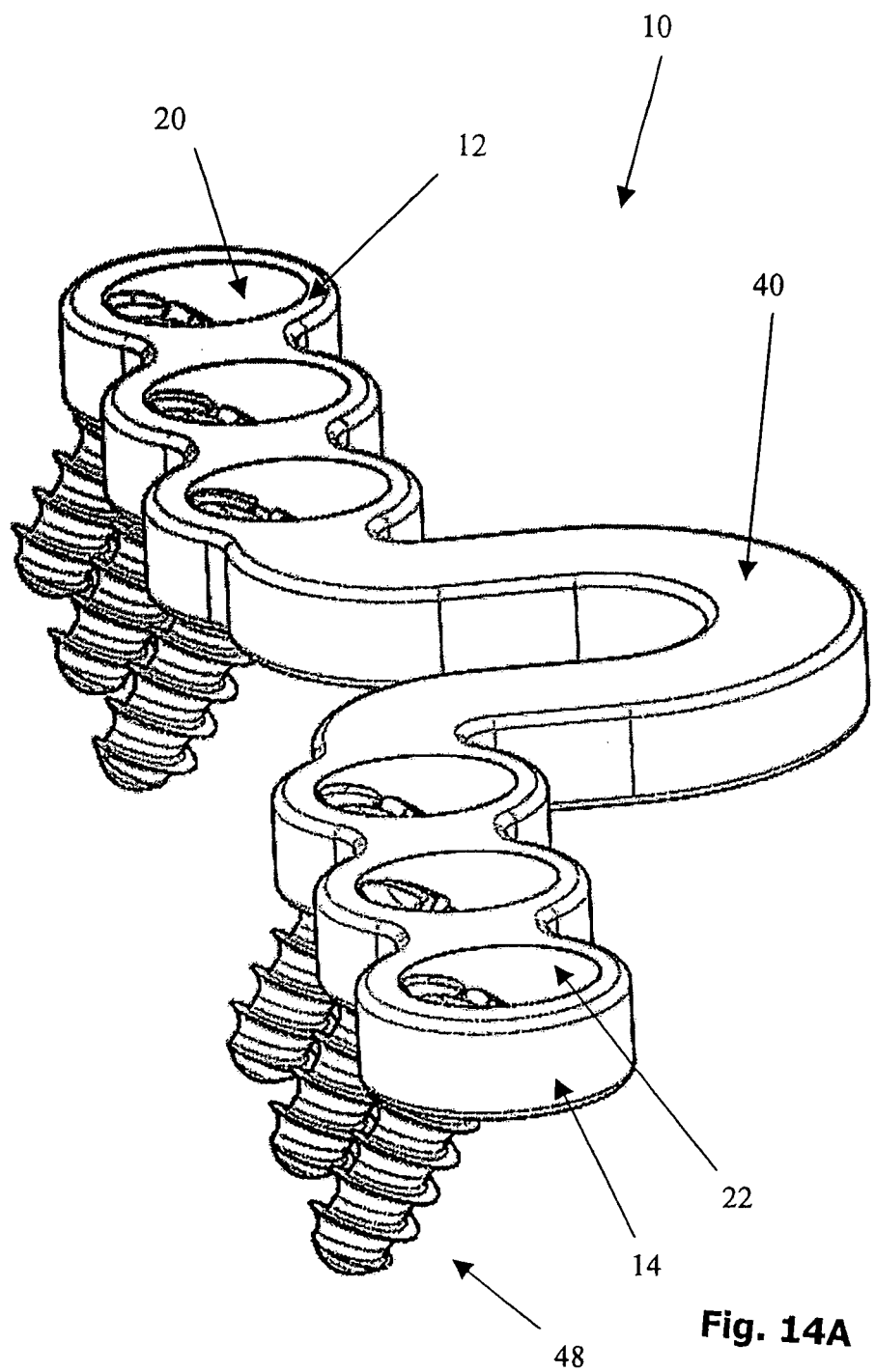
FIGS. 14A and 14B show two perspective views of a further osteosynthesis plate, in particular for treating jaw fractures.
Figure 14B:
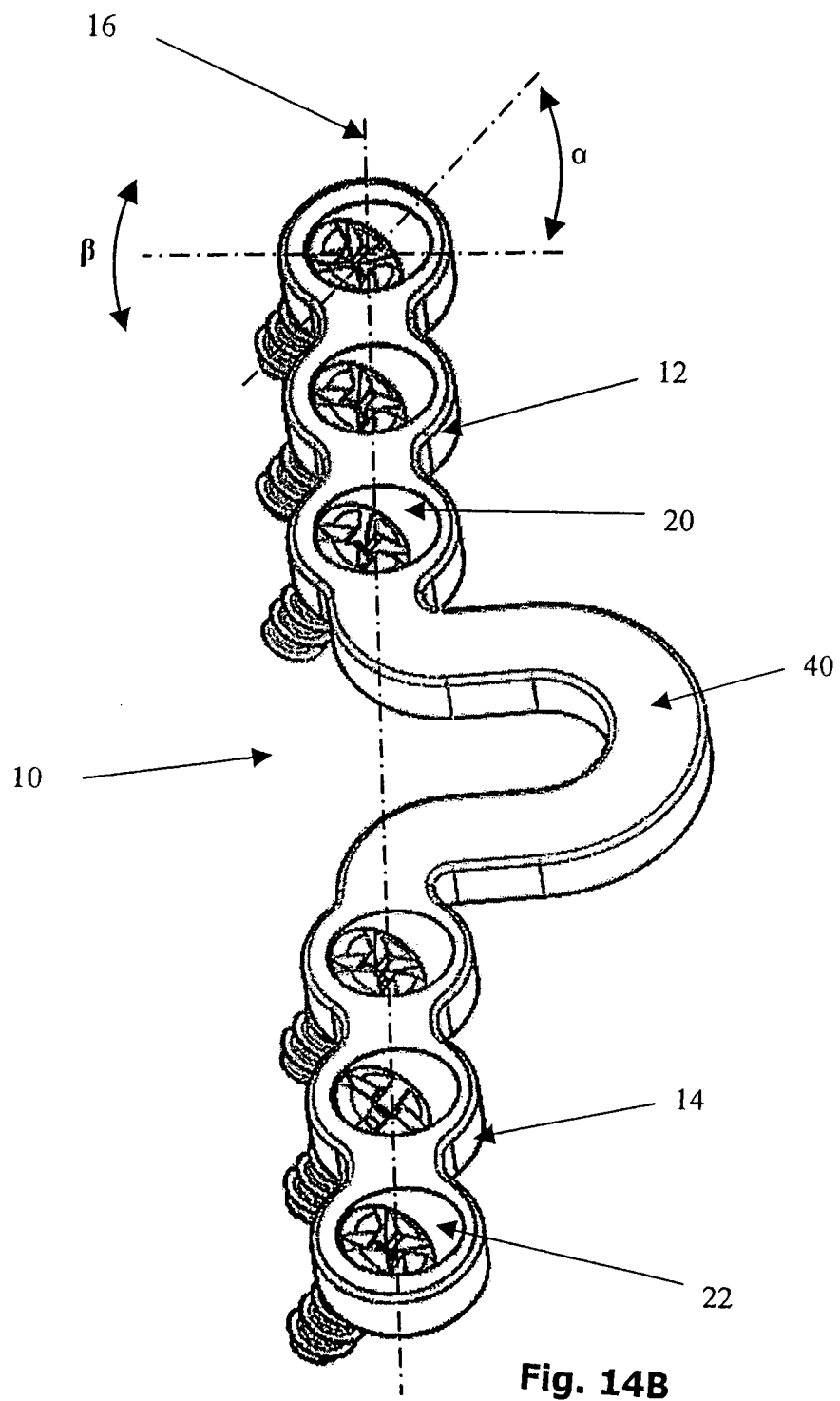

A further osteosynthesis plate 10 with two plate sections 12, 14 is illustrated in FIGS. 14A and 14B. The two plate sections 12, 14 have a common longitudinal axis 16 and are connected to one another via a meandering (U-shaped) bent connecting section 40. The osteosynthesis plate 10 can in the application state be positioned in such a way that the U-shaped bent connecting section 40 extends around a nerve. In a modification of the osteosynthesis plate 10 according to FIGS. 14A and 14B, at least one bone screw through opening is provided in the region of the connecting section 40.

The through openings 20, 22 intersect the plane of the plate in each case at an angle of inclination α=60°. The through openings 20 of the plate section 12 have within the plane of the plate an angular alignment β=90° with respect to the common longitudinal axis 16 (and in the direction of the free end of the plate section 12). The through openings 22 of the plate section 14 have an angular alignment β=270° with respect to the common longitudinal axis 16 and with respect to the free end of the plate section 14. The difference in the angular alignments of the through openings 20 and of the through openings 22 within the plane of the plate is consequently 0°.

FIGS. 14A and 14B show the osteosynthesis plate 10 in the base state. According to a further embodiment of the invention the osteosynthesis plate 10 can in the region of the connecting section 40 (which then acts as bending region) be deformed in such a way that the plate section 12 is inclined relative to the plate section 14.

Figure 15A:
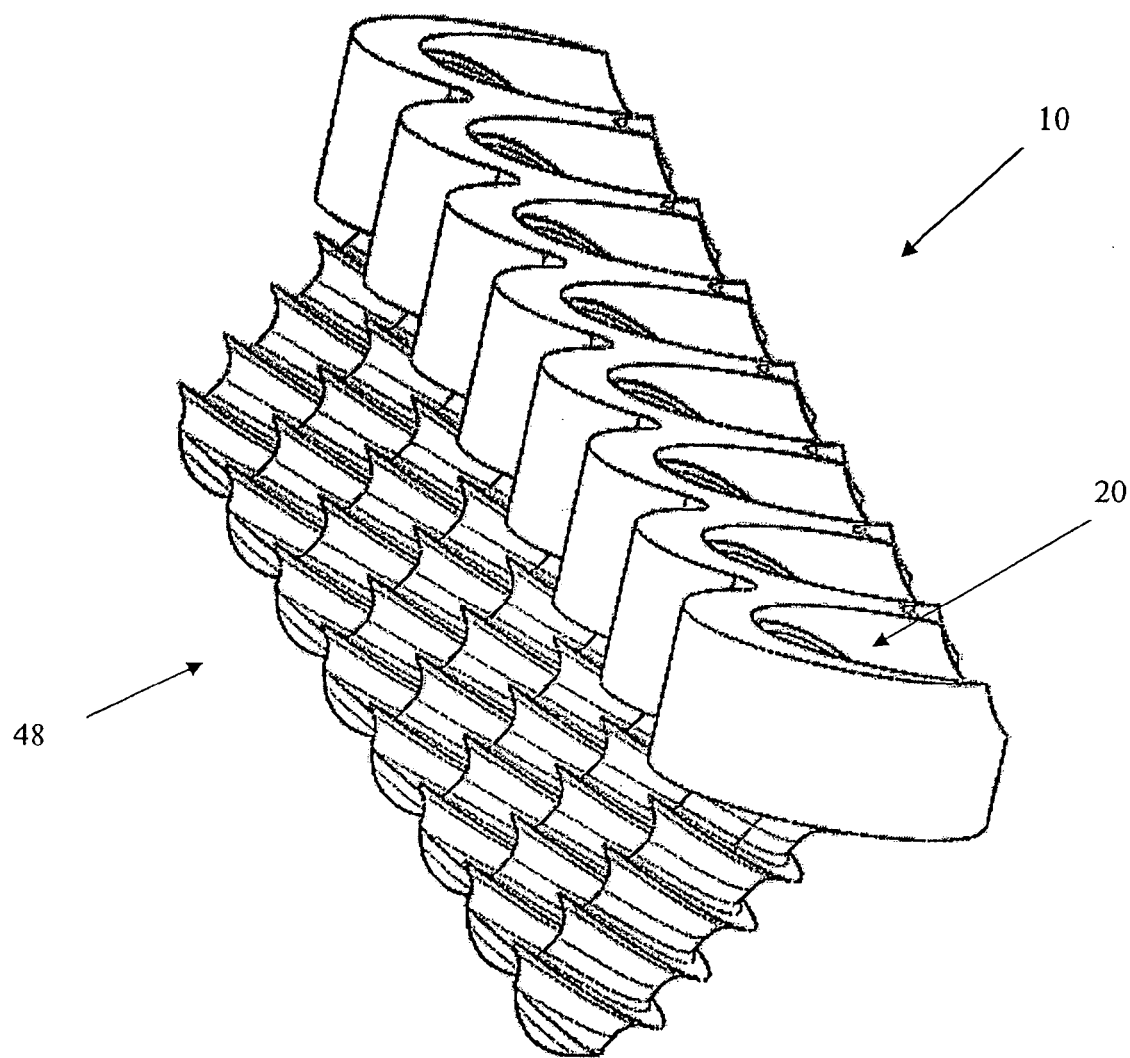
FIGS. 15A and 15B show in the linear base state and bent application state a further osteosynthesis plate, in particular for treating jaw fractures.
Figure 15B:
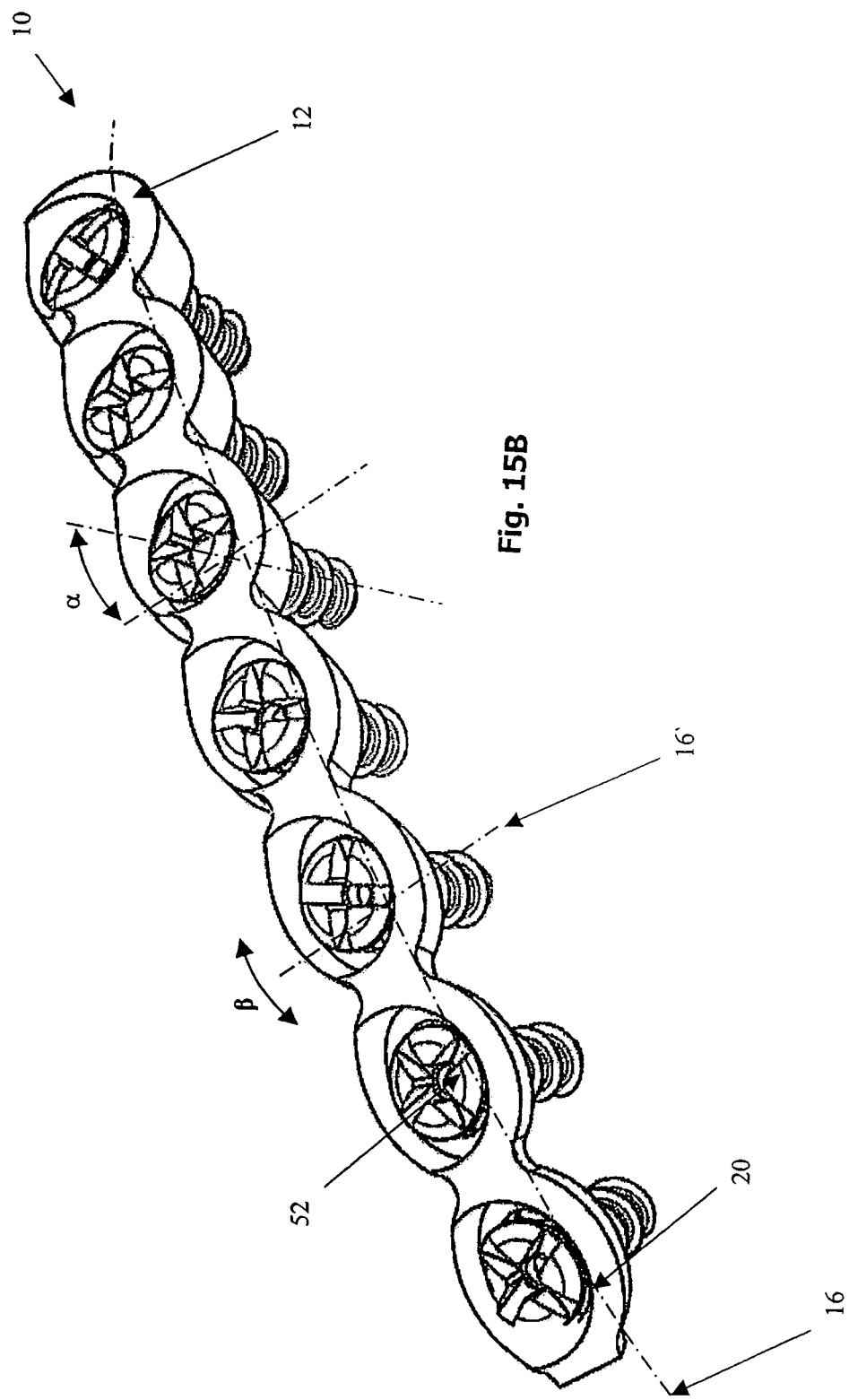

A further osteosynthesis plate 10 is illustrated in FIGS. 15A and 15B. The osteosynthesis plate 10 has in the base state illustrated in FIG. 15A a linear configuration with a total of eight through openings 20. The through openings 20 intersect the plane of the plate at an angle α=60° and have within the plane of the plate an angular alignment β=90°/270° (there is no preferred direction). The angular alignment β can vary by ±90°, preferably by approximately ±60°, with respect to the auxiliary line 16' shown in FIG. 15B.

FIG. 15B shows the osteosynthesis plate 10 in the bent application state. The osteosynthesis plate 10 is in this example secured in the region of the front side of the lower jawbone (therefore in the chin region) and its bent shape matches the contour of this bone. Since the through openings 20, 22 point inclined upwards, the screws 48 can be inserted intraorally (and in particular inclined from above).

The osteosynthesis plate according to FIGS. 15A, 15B can according to a further embodiment of the invention be deformed within the plane of the plate similarly as shown in FIG. 10, in such a way that two linear plate sections running parallel and staggered with respect to one another are formed.

A further osteosynthesis plate 10 is illustrated in FIG. 16. The osteosynthesis plate 10 has a linear configuration and comprises two plate sections 12, 14 connected to one another via a connecting section shaped as a bending region 30. The through openings 20, 22 of the plate sections 12, 14 have an angle of inclination α=60° with respect to the plane of the plate. The angular alignments of the through openings 20, 22 are in each case β=180° with respect to the free ends of the respective plate section 12, 14. The difference in the angular alignments of the through openings 20 and of the through openings 22 is accordingly 180°.

According to an embodiment of the invention the osteosynthesis plate 10 illustrated in FIG. 16 is bent at the site of the bending region 30 in such a way that the two plate sections 12, 14 are inclined to one another in a substantially V-shaped manner.

The osteosynthesis plates discussed with reference to FIGS. 1 to 11B are suitable for the intraoral treatment of fractures of the mandibular angle. The osteosynthesis plates described with reference to FIGS. 12A to 16 are suitable for the intraoral treatment of jaw fractures in jaw regions spaced from the mandibular angle, for example in the region of the chin or condylus.

The existence of two or more plate sections that are aligned non-linearly with respect to one another enables even complicated jaw fractures to be treated by means of a single osteosynthesis plate. The alignment of the individual through openings in the plane of the plate and perpendicular thereto is chosen in the embodiments in such a way that the osteosynthesis plates can be fastened in situ by an intraoral surgical intervention, i.e. through the mouth. No transbuccal access (i.e. through the cheek) is therefore necessary in order to place in position the osteosynthesis plates of the embodiments and secure them by means of suitable securement elements such as monocortical bone screws.

On account of the special alignment of the through openings the surgeon is able to place in position an osteosynthesis plate intraorally, carry out if necessary preliminary drillings, and then secure the osteosynthesis plate by means of several bone screws, all without the need for a transbuccal access. Conventional (longitudinally extended) straight instruments such as blades and drills are sufficient for carrying out these steps. The use of curved instruments can be dispensed with. A further advantage of the alignment of the through openings specified in the embodiments is the fact that the surgeon, despite the intraoral access, has a good field of view and can thus see exactly where he is drilling and where the bone screws are placed.

Although the invention has been described with the aid of several embodiments of osteosynthesis plates for treating jaw fractures, the osteosynthesis plates according to the invention are also suitable for minimal invasive treatment of other fractures in the head region (for example the face).

On the basis of the above description and discussion the person skilled in the art will be able to employ numerous changes, additions and modifications that are still covered by the invention. The scope of protection of the invention is limited solely by the accompanying patent claims.

The invention claimed is:

1. An osteosynthesis plate for treating jaw fractures, comprising:
   in a plane of the plate, a linear first section with a first longitudinal axis and the linear first section extending substantially within the plane of the plate;
   a linear second section with a second longitudinal axis and the linear second section extending substantially within the plane of the plate and inclined to the first section;
   a plurality of first circular unthreaded through openings in the first section which are inclined to the plane of the plate and each of the first through openings have a first angular alignment within the plane of the plate with respect to the first longitudinal axis; and
   a plurality of second circular unthreaded through openings in the second section which are inclined to the plane of the plate and each of the second through openings have a second angular alignment within the plane of the plate with respect to the first longitudinal axis of the first section, wherein the first and second angular alignments differ with respect to the first longitudinal axis from one another by less than about 60°, so fastening elements can be introduced into the through openings of both plate sections in a direction predetermined by a single access.

2. The osteosynthesis plate according to claim 1, wherein the first and the second angular alignments differ with respect to the first longitudinal axis from one another by less than about 45°.

3. The osteosynthesis plate according to claim 1, wherein the first angular alignment is inclined to the first longitudinal axis and/or the second angular alignment is inclined to the second longitudinal axis.

4. The osteosynthesis plate according to claim 1, wherein the first through openings intersect the plane of the plate at an angle of approximately 20° to 80°.

5. The osteosynthesis plate according to claim 1, wherein the second through openings intersect the plane of the plate at an angle of approximately 20° to 80°.

6. The osteosynthesis plate according to claim 1, wherein the first angular alignment with respect to the first longitudinal axis is between approximately +90° and −90°.

7. The osteosynthesis plate according to claim 1, wherein the second angular alignment with respect to the second longitudinal axis is between approximately 60° and 180°.

8. The osteosynthesis plate according to claim 1, wherein the second angular alignment with respect to the second longitudinal axis is between approximately 180° and 300°.

9. The osteosynthesis plate according to claim 1, wherein the first section and the second section directly adjoin one another.

10. The osteosynthesis plate according to claim 1, wherein the first section has an angle of approximately 90° to 160° with respect to the second section.

11. The osteosynthesis plate according to claim 1, wherein the osteosynthesis plate comprises at least one bending region of reduced plate thickness and/or of reduced plate width and/or of meandering shape.

12. The osteosynthesis plate according to claim 1, wherein the first section has a length between approximately 5 and 70 mm and/or the second section has a length between approximately 5 and 70 mm.

13. The osteosynthesis plate according to claim 1, wherein the osteosynthesis plate in the region of the first section and/or in the region of the second section has a maximum plate thickness between approximately 0.5 and 3.5 mm.

14. The osteosynthesis plate according to claim 1, wherein the first through openings have underneath a plate surface a stop means for a head of a fastening element.

15. The osteosynthesis plate according to claim 1, wherein the second through openings have underneath a plate surface a stop means for a head of a fastening element.

* * * * *

UNITED STATES PATENT AND TRADEMARK OFFICE
CERTIFICATE OF CORRECTION

| | | |
|---|---|---|
| PATENT NO. | : 8,672,981 B2 | Page 1 of 1 |
| APPLICATION NO. | : 11/988225 | |
| DATED | : March 18, 2014 | |
| INVENTOR(S) | : Jacobs | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1089 days.

Signed and Sealed this
Twenty-first Day of July, 2015

Michelle K. Lee
*Director of the United States Patent and Trademark Office*